United States Patent
Aldestam et al.

[11] Patent Number: 5,807,245
[45] Date of Patent: Sep. 15, 1998

[54] SYNCHRONIZATION OF MEASUREMENT VALUES

[75] Inventors: Sten Aldestam, Lund; Göran Marnfeldt, Blentarp; Johan Waldeck, Södra Sandby, all of Sweden

[73] Assignee: Astra Aktiebolag, Sodertalje, Sweden

[21] Appl. No.: 563,199

[22] Filed: Nov. 27, 1995

Related U.S. Application Data

[63] Continuation of PCT/SE95/00556, May 17, 1995.

[51] Int. Cl.⁶ ............................................. A61B 5/04
[52] U.S. Cl. ............................... 600/300; 600/529
[58] Field of Search ................... 128/630, 637, 128/638, 716, 720, 721, 723, 725–728, 737–733, 739–741, 920, 923, 901; 600/509

[56] References Cited

U.S. PATENT DOCUMENTS

| | | |
|---|---|---|
| 4,803,625 | 2/1989 | Fu et al. . |
| 5,126,937 | 6/1992 | Yamaguchi et al. . |
| 5,138,552 | 8/1992 | Weedon et al. . |
| 5,316,009 | 5/1994 | Yamada .................................. 128/720 |
| 5,349,962 | 9/1994 | Lockard et al. ........................ 128/731 |
| 5,381,804 | 1/1995 | Shambroom ........................... 128/731 |
| 5,513,647 | 5/1996 | Castile ................................... 128/720 |
| 5,553,609 | 9/1996 | Chen et al. ............................. 128/630 |

FOREIGN PATENT DOCUMENTS

| | | |
|---|---|---|
| 0 498 909 B1 | 2/1991 | European Pat. Off. . |
| 0 505 627 A2 | 11/1991 | European Pat. Off. . |
| WO 95/33184 | 12/1995 | WIPO . |

*Primary Examiner*—Jennifer Bahr
*Assistant Examiner*—Stephen Huang
*Attorney, Agent, or Firm*—Fish & Richardson P.C.

[57] ABSTRACT

A measurement system including a first unit that obtains a first measurement value associated with a first time indication and a second measurement value associated with a second time indication and a second unit that comprises a processor and receives values asynchronously from the first unit, wherein the processor synchronizes the first and second measurement values using the first and second time indications.

26 Claims, 5 Drawing Sheets

SYNCHRONIZATION OF MEASUREMENT VALUES

CROSS REFERENCE TO RELATED APPLICATIONS

This is a continuation-in-part of International Application PCT/SE95/00556, with an International filing date of May 17, 1995.

REFERENCE TO MICROFICHE APPENDIX

A computer program listing is included in a Microfiche Appendix hereto.

BACKGROUND OF THE INVENTION

The present invention relates to a measurement system which includes a central processor unit connected to at least one satellite sensor unit for obtaining measurement values. Furthermore, the invention concerns a method for processing measurement values.

Most prior-art measurement systems include one or more sensors, which measure parameters of interest, and a processing unit, which processes the measured values of the parameters before display. For instance, U.S. Pat. No. 5,126,937, incorporated herein by reference, relates to a biological information measurement system including multiple measuring sections connected to a processing unit, which adjusts values obtained by some of the measuring sections to take into account temperatures measured by others of the measuring sections, and which sends the adjusted values to a display unit and a recorder. Another example, U.S. Pat. No. 4,803,625, also incorporated herein by reference, describes a processor-based monitor that gathers patient information which is transmitted to a central computer for display and storage.

In many instances, a parameter of interest that cannot be measured directly must be calculated on the basis of other measured values and according to a mathematical model. For example, pulmonary compliance, monitored to study a patient's response to a new drug, is by its nature a derived value that must be calculated on the basis of respiratory airflow and pulmonary pressure.

The mathematical models involved are sometimes complex, leading to time-consuming calculations which have to be performed in several steps using measurement values from different sensors. Presenting the results in real time typically requires parallel execution of some steps. A synchronous system must take into account that some of the parallel-executing steps may not have the same execution times as others. By starting a later dependent calculation step prior to completion of the calculations of previous steps, an incorrectly-designed system may lose the time information inherent in the measurement values and therefore work out of step, yielding incorrect results.

In addition, a measurement system tailored for a particular application to take into account the specific execution times required for the different calculations involved is typically time-consuming, expensive to use, and suitable for one application only.

Another typical problem of measurement systems, especially those used for research and development, relates to the documentation of the experiments performed. According to good laboratory practice, all pharmacological experiments must be documented in such a way as to provide for repetition. However, while the primary measurement data and the results of any related calculations are typically stored automatically on a diskette or the like, the experimental procedure, including, e.g., which sensors were used with which calibration factors, is typically recorded manually by the researcher, which may result in errors.

SUMMARY OF THE INVENTION

The invention provides a measurement system in which measurement values obtained are associated with time indications so that the values can be processed asynchronously and then re-synchronized later to produce accurate derived measurement values. In particular, the invention provides a measurement system including a first unit that obtains a first measurement value associated with a first time indication and a second measurement value associated with a second time indication, and a second unit that comprises a processor and receives values asynchronously from the first unit, wherein the processor synchronizes the first and second measurement values using the first and second time indications.

The meaning of "associating," as used herein, means linking by, e.g., juxtaposing in memory or including together in a packet of data. The "second," "third," and "fourth" memories described herein can be not only separate memory arrays but also, e.g., merely different positions in a single database or memory array. Furthermore, "time indication," as used herein, means a timestamp value representing a particular moment in time, such that multiple separate time indications can have the same timestamp value, i.e., point to the same moment in time. In addition, a "first unit" as described herein can be not only a single first unit obtaining both first and second measurement values, but also, e.g., a set of two first units wherein one first unit obtains the first measurement value and the other first unit obtains the second measurement value.

BRIEF DESCRIPTION OF THE DRAWINGS

Embodiments of the invention will now be described with reference to the accompanying drawings, in which.

DETAILED DESCRIPTION

A measurement system according to the invention provides specialized software running on commercially-available hardware equipment making use of standard measurement gauges and instruments. Although the system uses multiple levels of processors all running different programs, specific time indications showing when measurements are made at the most basic level are preserved and used at all levels to maintain accuracy. The hardware discussion below is followed by a description of the software.

System Hardware

Figure 1:
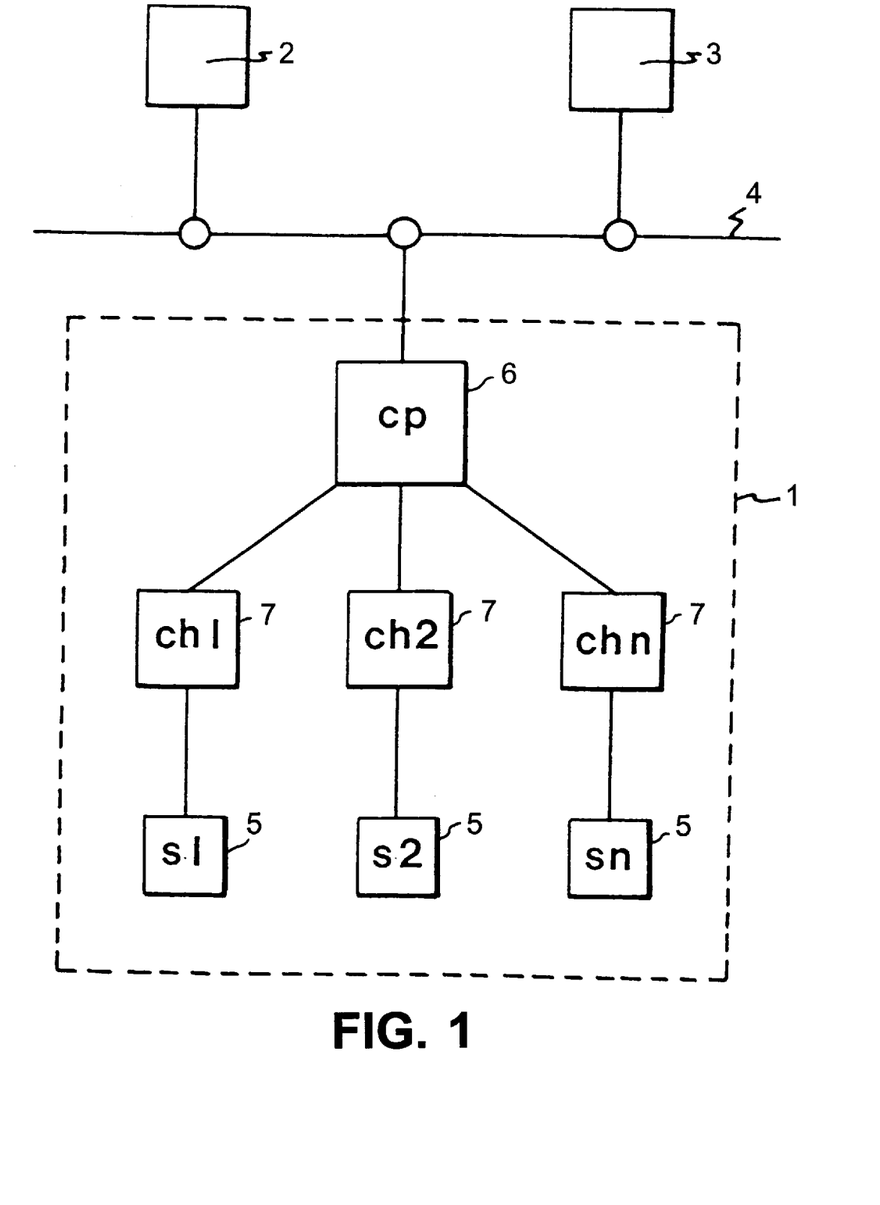
FIG. 1 is an overview schematic block diagram of the hardware of measurement system according to the present invention.

As shown in FIG. 1, a measurement system according to the invention provides a measurement computer 1 (dashed outline), a workstation 2, and a database 3, all of which are connected to a data network 4. The measurement computer 1 itself includes various units including one or more sensor units 5, each of which is connected to a processor unit 6 via respective channel units 7. In this embodiment, the "first unit" includes the sensor units 5a, 5b and the channel units 7, whereas the "second unit" includes the processor unit 6.

Figure 2:
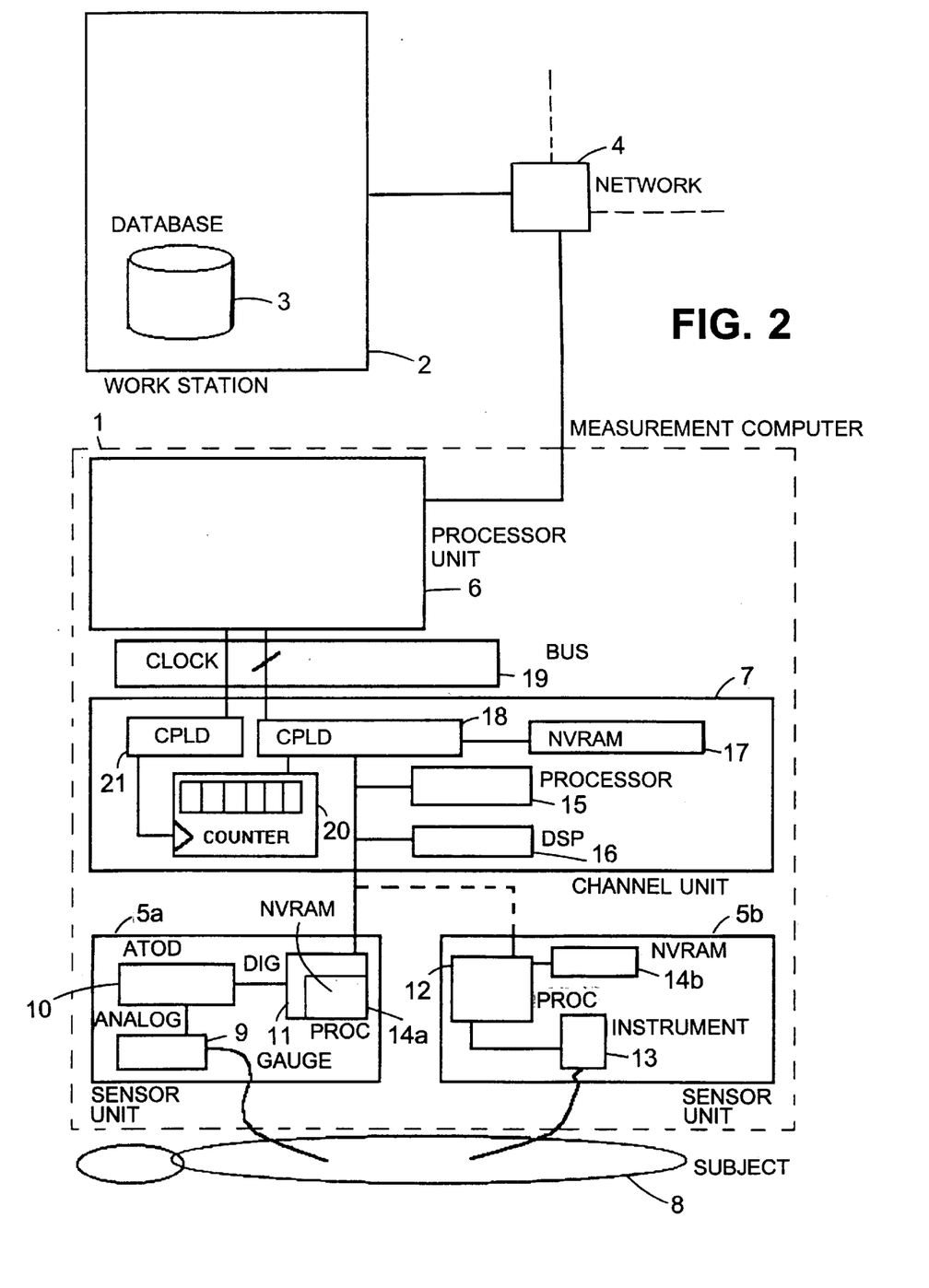
FIG. 2 is a more detailed schematic block diagram of the hardware of a measurement system according to the present invention.

The system hardware can be implemented using standard off-the-shelf system-level components. With reference to FIG. 2, the following describes an example of such an implementation in which the database 3 is housed within the workstation 2. The sensor units 5a, 5b, coupled to a test subject 8, e.g., a laboratory animal, for measuring different parameters, can use different kinds of gauges 9, e.g., a pressure gauge, a temperature gauge, or a flow gauge.

One type of sensor unit 5a includes not only an analog-to-digital converter 10 connected to the gauge 9 for digitizing the analog values measured by the gauge 9, but also a processor 11, e.g., a Motorola M68HC711E9, and a non-volatile memory (NVRAM) 14a which can be included in the processor 11 as shown in FIG. 2. The processor 11 operates on the measurement values by, for example, scaling to System International units, and also communicates with the associated channel unit 7 via a connection using a protocol such as RS-422.

Another kind of sensor unit 5b includes instead a processor 12 such as a Motorola M68302FE16 which connects to a pH meter or other commercially-available instrument 13 via an RS-232 connection or the like. The processor 12 also stores an identity code in a non-volatile memory 14b such as XICOR 24C16E2PROM, and also communicates with its associated channel unit 7 via an RS-422 or similar type of connection.

Each channel unit 7 includes a processor 15, e.g., a Motorola MC68HC000P16, and a digital signal processor (DSP) 16, such as an AT&T WEDSP32C, which run programs to perform calculations using only measurement data from the associated sensor unit 5a, 5b. Such calculations include filtering and averaging and more complex functions. Thus, the channel units 7 reduce the amount of primary data that the processor unit 6 must store and process. However, if there is no need for such a reduction, the above-mentioned calculations by the channel units 7 can be performed by the processor unit 6 instead.

Each channel unit 7, which includes a non-volatile memory 17 such as the aforementioned X24C16E2PROM for storing a serial number and communicates via an RS-422 or similar connection with the associated sensor unit 5a, 5b, is connected by a Complex Programmable Logic Device (CPLD) 18 to the processor unit 6 using a common bus 19 such as VME.

The processor unit 6, a Motorola XC68040HRC25E processor-based Force Sys68K CPU-40B/4 main board or the like, is connected to a network 4, e.g., Ethernet, link for communication with the workstation 2 and performs calculations requiring measurement data from different sensor units 5a, 5b or channel units 7 or both.

For time synchronization and generation of time indicators, each channel unit 7 includes a clock or register counter 20, implemented using another CPLD 21, to obtain a time indication for each sampled measurement value. More particularly, the processor unit 6 provides on the common bus 19 a clock signal used to increment and thus synchronize all the counters 20. The CPLD 21, dividing the clock signal into various sampling frequencies, e.g., 16 Mhz into 1000, 500, 200, 100, 50, 20, 10, 5, 2, and 1 Hz, uses one of the frequencies, e.g., 1000 Hz, to increment the counter 20 from which the time indications are obtained. When an experiment is started, the processor unit 6 writes to a specific address on the common bus 19, which resets all of the counters 20, one for each sensor unit, to ensure that all begin at the same count. Thus, although the time indication associated with each measurement value is initially relative, the absolute time of measurement can be established by reference to the time of reset.

The sensor units 5a, 5b the channel units 7, and the processor unit 6 are all processor-and-memory-based units, each of which can be adapted to perform different operations in accordance with a downloaded program. To this end, each unit in the measurement computer 1 is given a unique identity code, which is stored in a non-volatile memory 14a, 14b, 17. When the system is turned on, the processor of each unit reads its identity code from a non-volatile memory 14a, 14b, 17. Each unit then requests a program by transmitting the identity code to the processor unit 6, which in turn requests the program from the database 3 where all programs applicable in the measurement computer 1 are stored. After receiving the programs from the database 3, the processor unit 6 downloads them into the channel units 7 and the sensor units 5a, 5b.

In addition to storing all of the programs, the database 3 also stores for each unit in the measurement computer 1 a description including, for instance, the unit's identity code, the kind of gauge 9 a sensor unit 5a, 5b uses, the measurement range of the gauge 9, and the scaling factors involved. Furthermore, the database 3 contains a description of all of the measurements that can be carried out by the measurement system. Such a description defines which programs are to be used in the different units of the measurement computer 1, which data streams are directed into and directed from the programs, and which data streams are to be displayed at the workstation 2.

When a particular measurement is to be carried out, the hardware is set up for use as follows. First an operator at the workstation 2 selects the name of a measurement to be made. The appropriate application program is then downloaded into the measurement computer 1 from the database 3. The operator also specifies the parameters for the experiment for which the measurement is to be performed, e.g., doses of a drug to be given to the test subject 8. Furthermore, the operator can calibrate the gauges 9 of the sensor units 5a, 5b from the workstation 2, the calibration factors being automatically stored in the database 3. In addition, all of the information entered from the workstation 2 is stored in the database 3.

This configuration method has many advantages. First, the operator is able to carry out the experiment easily in the particular way intended. Second, the experiment is adequately documented for later repetition, since all of the information entered is stored in the database 3. Third, the measurement system can be operated only from the workstation 2, which ensures that all steps taken are automatically documented and provided with a time notation. Finally, if a wrong sensor unit 5a, 5b is connected to a certain channel unit 7, so that the hardware configuration of the measurement computer 1 does not correspond to the description in the database 3, the system will discover the erroneous coupling using the identity code.

The operator can also configure the system for new measurements by entering a description of the new configuration at the workstation 2. Stored in the database 3, the description of the new configuration can be selected for use at a later stage.

System Software

Operating with hardware such as that noted above, the software can be described as separate action processes, i.e., programs, connected by data streams, wherein each stream is buffered by the process receiving it. By combining different processes, different measurement applications can be implemented. In the following very simple application example, a first channel unit (kanal 0) produces one output data stream, "chn 0," and a second channel unit (kanal 1) produces two output data streams, "min 1" and "max 1." These streams are directed to a process in the processor ("main") unit, which in turn produces an output data stream of sums.

```
define kanal 0 (chn__0);
end kanal 0;
define kanal 1 (chn__1);
    minmax (chn__1); => (min__1, max__1);
end kanal 1;
define main;
    add (min__1, chn__0) => (summa);
end main;
```

Figure 3:
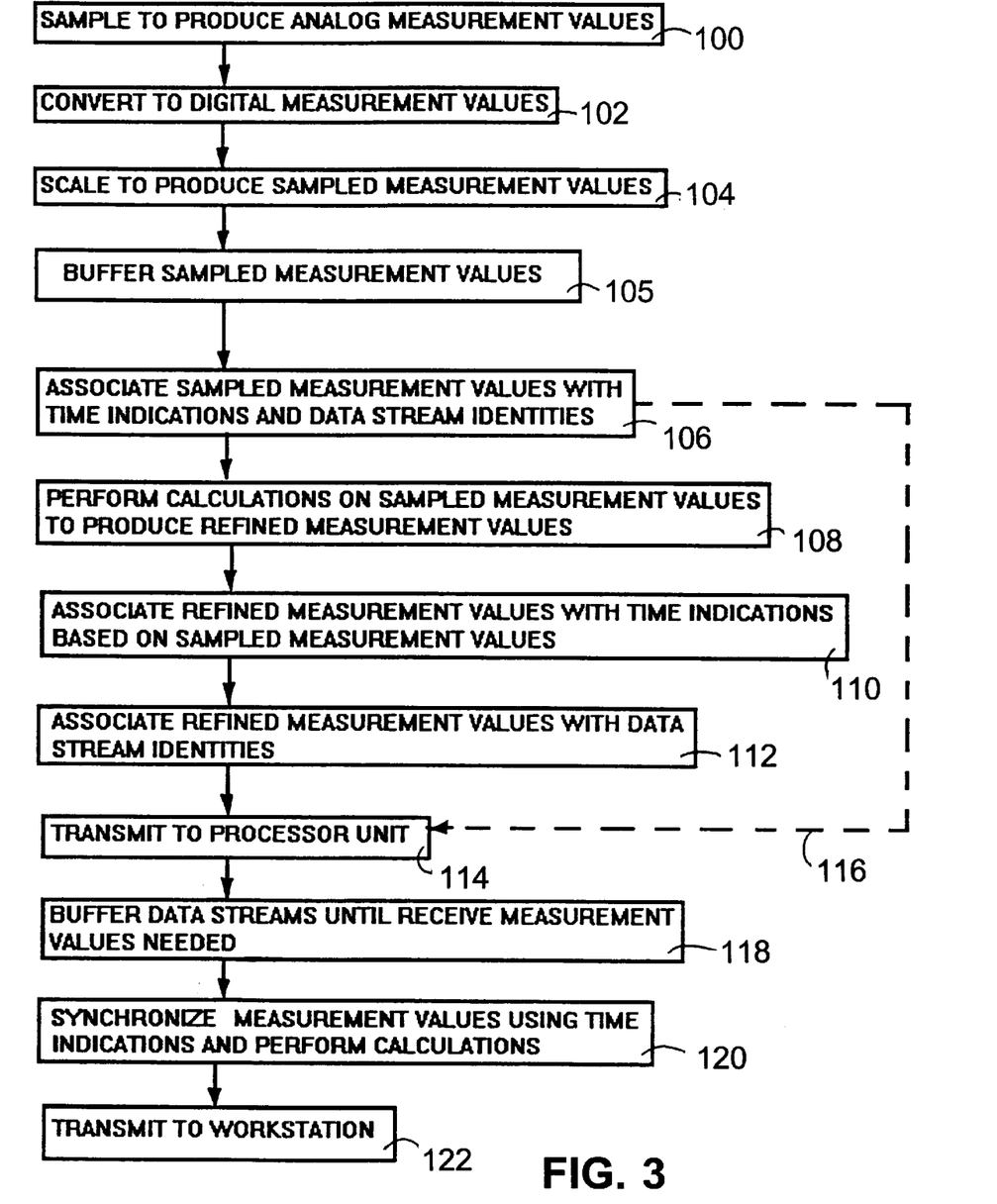
FIG. 3 is a flowchart illustrating the steps of a measurement method according to the present invention.

Referring now to FIGS. 2 and 3, the system software flows as follows. The gauge 9 of a sensor unit 5a, 5b samples a parameter to produce "analog measurement values" (step 100), which are then converted to "digital measurement values" for feeding into the processor 11, 12 of the sensor unit 5a, 5b (step 102). The processor 11, 12 of the sensor unit 5a, 5b scales the digital measurement values to System International units and forwards the resulting "sampled measurement values" to the associated channel unit 7 (step 104), where the "sampled measurement values" are buffered (step 105). In the channel unit 7, each sampled measurement value is associated with not only a time indication obtained from the counter 20 and representing the time at which the measurement value was sampled, but also a data stream identity, defining the parameter sampled by the gauge 9 (step 106).

Each channel unit 7 then performs calculation programs, e.g., filtering, which require only sampled measurement values from the associated sensor unit 5a, 5b (step 108). The output from each of the calculation programs constitutes a stream of "refined measurement values." The processor 15 of the channel unit 7 adds a time indication to each of the refined measurement values in the output stream (step 110). The purpose of this time indication is to indicate a time origin of the refined measurement value. Thus, multiple refined measurement values originating from either (1) multiple sampled measurement values created at the same time by different sensor units 5a, 5b, or (2) just one sampled measurement value, e.g., filtered and average values derived from the same sampled value, can be synchronized later. This ability is especially important when refined measurement values, having been subjected to different processes of varying durations, have lost their initial inherent synchronization. The time indication which is associated with a certain refined measurement value is usually the time indication associated with the corresponding sampled measurement value input to the calculation program. However, the time indication can instead represent a time between two actual sampling times, e.g., when the calculation is an interpolation or is selected from among the time indications of multiple sampled measurement values. In any case, the time indication of a refined measurement value is derived from the time indication(s) of one or more of the corresponding sampled measurement values. The means for determining the time indication of the refined measurement value can be a part of the calculation programs.

The processor 15 of the channel unit 7 also adds to each of these refined measurement values a "data stream identity" defining the parameter obtained by the calculations (step 112). The stream of refined measurement values resulting from the processing in the channel unit 7 is transmitted to the processor unit 6 (step 114). In addition, the stream of sampled measurement values received by the channel unit 7 or any stream of measurement values resulting from an intermediary calculation step, or both, can be transmitted to the processor unit 6, if needed for the calculation steps performed therein, or if to be used as an output from the measurement computer 1 (step 116).

Usually, different channel units 7 require different amounts of time for processing. Accordingly, the refined measurement values received at the same time by the processor unit 6 from the different channel units 7 are often unsynchronized, i.e., have different time indications. The same is true for measurement values which are received at one time from a single channel unit 7 or sensor unit 5a, 5b, and are derived from the same original measurement values, but which may be the result of asynchronous processing of these values.

To enable calculations that use synchronized measurement values, the processor unit 6 buffers the data streams until all measurement values with corresponding time indications, and required for a specific calculation, have been received (step 118). The processor unit 6 then uses the time indications to synchronize corresponding measurement values from different data streams (step 120).

The processed data streams resulting from the calculations in the processor unit 6 are transmitted with other selected data streams to the workstation for display in real time and to the database 3 for storage (step 122). Thus the time indications permit measurement values obtained by different sensor units 5a, 5b at the same time to be displayed at the same time. The stored data include measurement values, either processed or as sampled, together with their associated time indications and their data stream identities.

EXAMPLES

Figure 4:
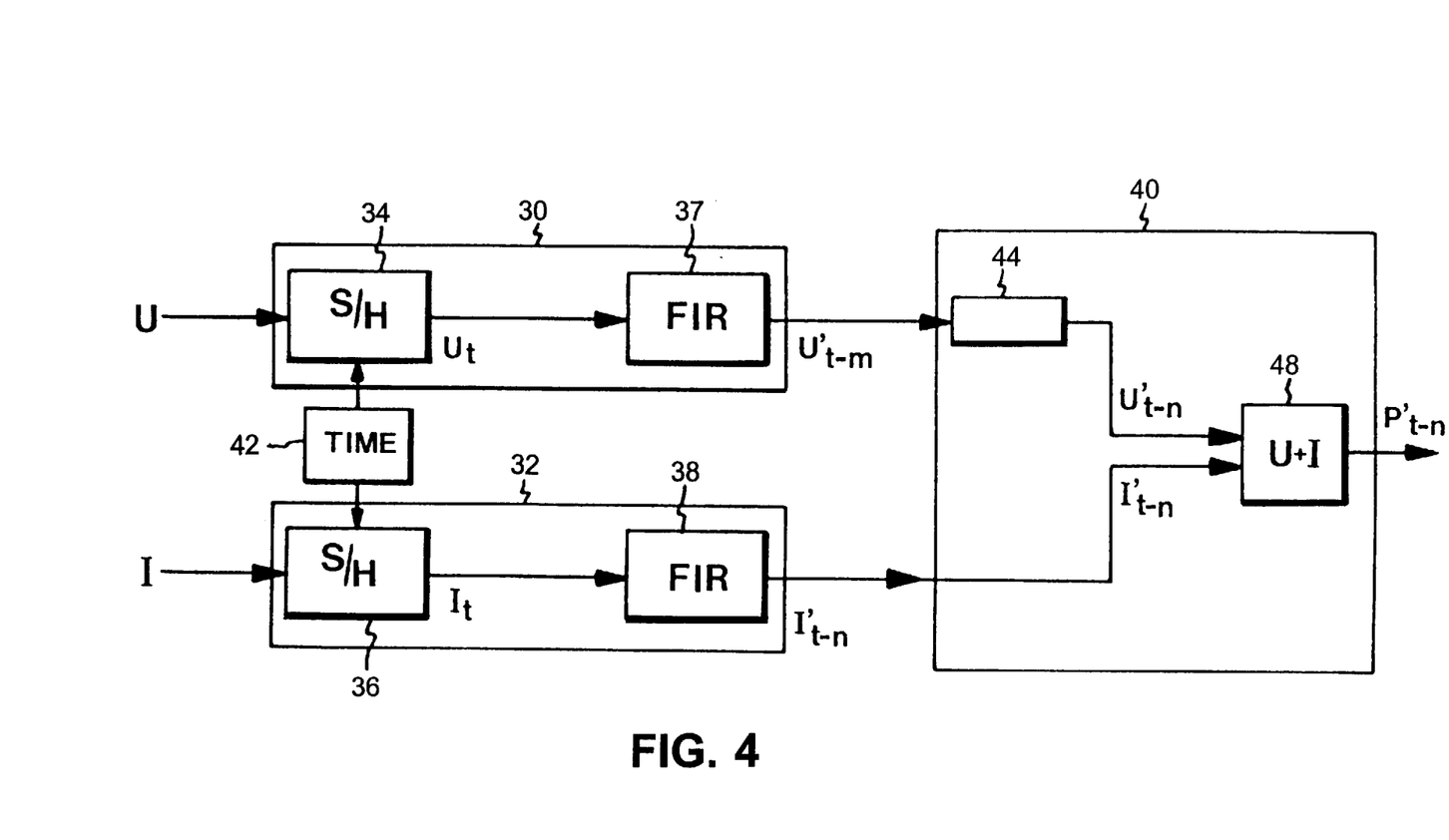
FIG. 4 is a schematic block diagram illustrating a measuring method according to the present invention as applied to the measurement of power.

FIG. 4 shows an example of how the invention can be applied to measure power and produce a data stream of power values. In this case, the measurement system has a first sensor unit 30 and a second sensor unit 32, each of which includes a sample-and-hold circuit, i.e., analog-to-digital converter 34, 36 and an FIR-filter 37, 38. Here, while there is a processor unit 40 for calculating the momentary value, the channel unit functions of (1) associating a time indication and a data stream identity with a sampled measurement value and (2) filtering the sampled measurement value are merged into the sensor units 30, 32. Each of these two sensor units 30, 32 forms a so-called "first unit."

The first analog-to-digital converter 34 samples a voltage. The voltage value sampled at time t is designated Ut. The analog-to-digital converter associates the time indication t, obtained from a clock register or counter 42, and a data stream identity "sampled voltage" with the voltage sample Ut. Similarly, the second analog-to-digital converter 36 samples, at time t, a current I. A time indication t from the counter 42 and a data stream identity "sampled current" are also associated with the current sample It.

The first FIR filter 37 has a length of 2 m. Thus, the output of the FIR filter 37 depends of the values of 2 m voltage samples. The filtered voltage value output at time t from the first FIR filter 37 is designated U't-m—a time indication t-m is associated therewith to indicate that U't-m substantially represents the voltage at time t-m. Furthermore, a data stream identity "filtered voltage" is associated with the filtered voltage value.

Correspondingly, the second FIR filter 38 has a length of 2 n and its output depends on the values of 2 n current samples. The filtered current value output at time t by the second FIR filter 38 is designated I't-n. A time indication t-n and a data stream identity "filtered current" are associated with the filtered current output. If m is shorter than n, the delay created by the first FIR filter 37 is shorter than that created by the second FIR filter 38. Thus, the filtered voltage value U't-m is available earlier than the corresponding filtered current value I't-m. So the filtered voltage values are queued in a buffer 44 in the processor unit 40. This processor unit 40 forms the so-called "second unit" in this embodiment.

At time t, detecting the availability of both a filtered voltage value U't-n and a filtered current value I't-n having the same time indication t-n, a calculation program 48 in the processor unit 40 produces the power value Pt-n. In addition, the calculation program 48 associates the time indication t-n and a data stream identity "power" with the calculated power value which then represents the power measured at time t-n. Additional power values are derived in turn in the same manner, which produces a "power" data stream of values.

Figure 5:
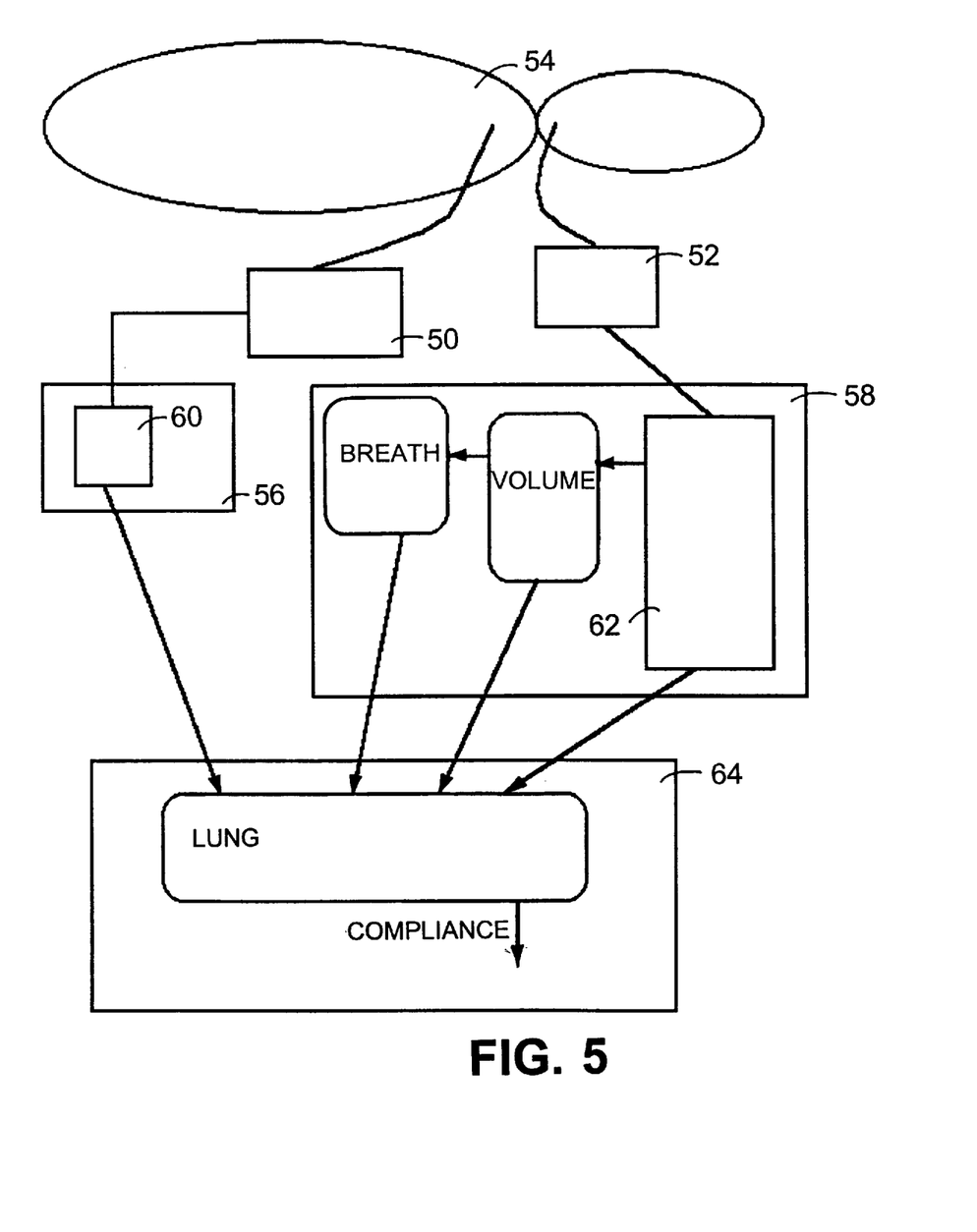
FIG. 5 is a schematic block diagram illustrating a measuring method according to the present invention as applied to the measurement of pulmonary compliance.

In another example, shown in FIG. 5, the system is configured to measure pulmonary compliance according to the brief, self-explanatory program listing below.

```
application "Pulmonary_mechanics";
    define kanal 0 (pressure_raw);
        1p_filter (pressure_raw) => (pressure);
    end kanal 0;
    define kanal 1 (airflow_raw);
        1p_filter (airflow_raw)    =>    (airflow);
        volume (airflow)           =>    (volume);
        breath (volume)            =>    (breath_trigger);
    end kanal 1;
    define main;
        lung (pressure, airflow, volume, breath_trigger)
            => (compliance);
    end main;
```

A first sensor unit 50 and a second sensor unit 52 sample a pulmonary pressure and a respiratory airflow, respectively, of a laboratory animal 54, whereby a data stream of pressure values and a data stream of airflow values are generated. These streams and others derived in the development of the compliance measurement are all buffered by the programs receiving them in the following steps.

The pressure and airflow data streams are filtered in a first channel unit 56 and a second channel unit 58, respectively, by digital signal processors 60, 62 which include filtering software modules. The stream of filtered pressure values is forwarded directly to the program "lung" running in a processor unit 64. Also forwarded to the program "lung," the stream of filtered airflow values is directed as well to the channel unit 58 program "volume," which integrates the airflow values to obtain a stream of volume values. Together, the sensor units 50, 52 and channel units 56, 58 form the so-called "first unit."

Likewise, the stream of volume values is directed not only to the "lung" program but also to another channel unit 58 program "breath," which detects the beginning of an inhalation by the animal 54 and creates a stream of "breath_trigger" values which is directed to the "lung" program. Thus, asynchronously processed values of the various streams determined at the same time arrive at the "lung" program at different times. However, as described above, the values are synchronized using their associated time indications, allowing the "lung" program to calculate compliance accurately for display or storage.

The microfiche appendix which is incorporated herein by reference, is a listing which includes software routines written in the Modula-2 software language, a compiler for which is available from various sources, including Introl Corporation, ACE Associated Computer Experts bv, and A+L AG. These software routines, self-explanatory to a programmer of ordinary skill in the art, describe a detailed example of how software according to the invention can be created. For example, the procedure "Get_samples" relates to synchronizing measurement values by reference to time indications, or time "stamps."

The following description, using terminology known to a practitioner of ordinary skill in the art, explains the listing of Appendix A in detail.

The three purposes of the "Applicat" module are (1) to provide primitives for handling streams of data samples between action processes, (2) to manage an application, that is, maintain data structures of action processes with qualifiers and stream connections between the action processes, and (3) to provide a programming interface for application modules containing action process routines.

"DEFINITIONS," i.e., declarations, are included first. The "Sample_type" record is the basic unit of a stream. The "Stream" fields identify the stream number from which a sample comes or to which it should be sent. The "stamp" field is a timestamp which indicates when the sample was created, by noting how many milliseconds have passed since the application was started. The "sample" field is the actual value of the sample. An action process or satellite sensor unit may be unable to generate a sample at a specific time, in which case the "missing" flag is set to so indicate. If the "missing" flag is set to true, the value in "sample" is undefined and should not be used.

All action processes retrieve information about connected streams and so on through the "Param_type" data structure which is retrieved by a "Sched.Get_parameter" procedure. The "stream_input" vector lists the numbers of the streams connected as inputs to the action process. The "stream_output" parameter similarly lists output stream numbers. The "buffer_input" vector contains references to the buffers of all of the input streams connected to this action process.

The following procedures are used in an application module. The procedure "Init_FIFO_record" initiates a "vector" structure with information about connected streams from a "param" structure. The "param" structure must be previously initiated with a "Sched.Parameter" procedure. The "FIFO_record" structure contains buffers and data structures needed by the "Put_sample" and "Get_samples" routines, described below.

The procedure "Get_samples" retrieves samples directed to the process as specified in the "vector" structure. When the procedure returns, the "samples" structure contains a new sample from each stream the process is reading. The incoming samples are synchronized so that the procedure does not return until samples from all streams are received. If necessary, the procedure "Get_Samples" returns samples for each timestamp value in the connected streams by duplicating the most recent sample in streams lacking a sample with the exact timestamp.

For example, three action processes A, B, and C may be connected so that A and B each generate a stream read by C. Process A generates the following two samples by calling the procedure "Put_Sample:" (value 1.0, stamp 10) and (value 2.0, stamp 30). Similarly, process B generates three samples: (value 3.0, stamp 20), (value missing, stamp 30), and (value 5.0, stamp 40). This is summarized in the following table:

| Stamp (ms) | Stream A | Stream B |
|---|---|---|
| 10 | 1.0 | |
| 20 | | 3.0 |
| 30 | 2.0 | missing |
| 40 | | 5.0 |

Process C can now call the "Get_samples" procedure three times, receiving the following values:

| Call | Stamp | Stream A | Stream B |
|---|---|---|---|
| 1 | 10 | 1.0 | missing |
| 2 | 20 | 1.0 | 3.0 |
| 3 | 30 | 2.0 | missing |

The first call to the procedure "Get_Samples" returns values for the lowest timestamp, i.e., 10 ms. Since there is no sample in stream B with lower timestamp than 20 ms, a value of "missing" is returned for stream B.

The second call retrieves values for timestamp 20 ms. Since the next available sample from stream A has timestamp 30 ms, the routine returns the previous value of 1.0 for stream A.

The samples for timestamp 40 ms cannot be returned until a new sample is received from stream A, because it is not yet known if the timestamp for the next sample from stream A is higher than 40 ms.

The "Put_sample" procedure puts one sample into the output stream. The "sample" record contains information such as the stream number and the sample value. The routine name for "caller" is specified to simplify debugging. The value of "sample.stamp" must be higher than the previous sample for the same stream.

The "Register_action" procedure is called in the main block of an application module to register each application, i.e., action process, defined in the module. "Name" represents the action process name that should be used to refer to the action process in an application description file. "Routine_proc" is the application process defined. The "stack_size" parameter determines how much memory to allocate for the process's stack.

The "Create_FIFO" procedure creates a new FIFO buffer for stream number "index" and is used when starting applications.

Used internally to initiate the data structures that keep track of the application processes and streams, the "Clear_application" procedure does not deallocate memory or stop processes.

The "Append_action" procedure, which inserts data from "reply" about a requested action process that will later be started by the "Start_application" procedure, is called from the load process when receiving an application description from the workstation.

The "Append_kanal_param" procedure inserts data from "reply" about a stream from a channel unit that will be set up when the application is started.

Storing the visibility flag for a stream, the "Append_visible" procedure causes the stream to be sent to the workstation when the application is started.

The "Start_process" procedure starts an action process and connects it to its streams.

Starting all action processes for an application, the "Start_application" procedure installs an "append_proc" procedure that will be called for every sample from a visible stream. Likewise, "Stop_application" stops all action processes.

The following program, an implementation of a simple action process that sums two input streams, and its subsequent explanation provide a context for descriptions of procedures listed under "IMPLEMENTATION MODULE" in the microfiche appendix hereto.

```
IMPLEMENTATION MODULE AppDemo;
IMPORT Applicat, Console, Sched, Types;
PROCEDURE Adder_process;
CONST  routine = "AppDemo.Adder_process";
       in_streams  =  2;
       out_streams =  1;
VAR    param   :  Applicat.Param_type;
       output  :  Applicat.Sample_type;
       vector  :  ARRAY [0 .. in_streams-1] OF
       Applicat.FIFO_record_type;
       sample  :  ARRAY [0 .. in_streams-1] OF
Applicat.Sample_type;
BEGIN
    Sched.Parameter (param);
    (*Initiate input streams*)
    Applicat.Init_FIFO_record (vector, param);
    (*Initiate output streams*)
    output.stream := param.stream_output [0];
    LOOP
        Applicat.Get_samples (vector, sample);
        output.stamp := sample [0].stamp;
        output.missing := (sample [0].missing OR sample
        [1].missing);
        IF NOT output.missing THEN
            output.sample := sample [0].sample + sample
            [1].sample;
        END;
END Adder_process;
BEGIN
    Applicat.Register_action ("ADD", Adder_process.
2*1024);
END AppDemo.
```

The action process "Adder_Process" first connects to its streams through the calls to "Sched.Parameter" and "Applicat.Init_FIFO_record." The stream field of the output sample must also be initialized.

The main loop has four phases:
1. Get input samples, i.e., execute "Get_samples".
2. Check for missing values. If "missing" is true for a sample, the sample's value may contain any number including a meaningless number. If this value is used in a calculation, the process will terminate with an error.
3. Calculate output sample.
4. Put the output sample in an action process designated to receive the sample, i.e., execute "Put_sample."

The module's initialization code registers the action process to make it available to the application.

To be useful, this application module must be recognized by the application file parser in the workstation program. Subsequently, a statement such as the following can be used to execute this application module noted above:

add(term1, term2)=>(sum)

The following is a short description of the data structures and routines listed under "IMPLEMENTATION MOD- ULE" in Appendix A. "Application_active," which indicates whether an application is running, is set by "Start_application" and is cleared by "Stop_application." Set to TRUE when all parts of an application are loaded correctly, "Application_valid" must be set to start an application. The "Action" array contains information about all action processes that participate in the loaded application—the "Append_XXX" procedures add records to the array and "Start_application" reads it.

The "App_stream" structure holds information about all streams in an active application. Each stream has a visible flag indicating whether the samples for the stream should be sent to the workstation. For each stream there is a set of buffers, one for each action process reading values from the stream. The "App_stream" structure contains pointers to these buffers.

"Buffer_FIFO" is a collection of pointers to all stream buffers for an application and is used by "Start_application" and "Stop_application." Also used by the "Start_application" and "Stop_application" procedures is "Pid_FIFO," which includes process identifiers ("PIDs") of all active processes.

"Action_count" represents the number of started action processes. "Action_routine_head" is a linked list of registered action process descriptions. "Append_proc" points to a routine that is called for each visible sample. "Debug_count" reflects the number of "Put_sample" calls for each stream.

"Remember_stream" stores the stream number in the process's data area for debugging purposes and "Forget_stream" removes it.

Both "Init_FIFO_record" and "Get_samples" are described above. For further illumination, "Get_samples" operates as follows. First, for all streams where "next" is empty, a sample from the stream buffer is moved into "next." Second, the oldest timestamp in "next" is moved to "oldstamp." Third, for all samples in "next" with this timestamp, the sample is moved to "previous." Fourth, the timestamp in "previous" is set to "oldstamp." Finally, "previous" is returned.

"Put_sample," also described above, operates as follows. The fields in the sample are checked; if the stream is visible, then "Append_proc" is called with the sample. For all action processes reading the stream, the sample is put into the stream input buffer of the action process.

Another routine described above is "Create_FIFO," which operates in the following way. After a new input buffer for stream number "index" is created, the buffer pointer is stored in "App_stream" for reference by "Put_sample" and "Stop_Application." The buffer pointer is also returned to the caller, i.e., "Start_application," for later access by "Get_samples."

With respect to "Register_action," also described above, the information is stored in a linked list, "Action_routine_head," for use by the "Append_XXX" procedures.

"Lookup_action" returns a pointer to the registered information on action process "name;" NIL is returned if "name" is not found in the list.

"Clear_application," mentioned above, initializes "App_stream." Also mentioned above, "Append_action" appends an action process to the application according to "reply." The information from "reply" is combined with registered information and stored in the global "Action" vector for use by "Start_application." Mentioned above as well is "Append_visible," which sets the visible flag in streams according to "reply."

The "Start_process" procedure mentioned above is mainly called from "Start_application." It creates and starts an action process. The procedure initiates the process parameter property using the "stream_input," "stream_output," and the qualifier parameters. A stream buffer is also created for each input stream.

"Start_application" and "stop_application" are mentioned above. "Init_debug" clears the put sample counter for all streams. "Show_streams_proc" is a console command which displays a listing of all active streams for debugging purposes. "Zero_streams_proc," also a console command, resets the sample counters for all streams.

Other Embodiments

The embodiments described above are but examples, which can be modified in many ways within the scope of the appended claims. For example, the invention also applies to a measurement computer containing only a single sensor unit, if this sensor unit creates at least two streams of measurement values that need to be synchronized at a later stage in the measurement system. Furthermore, the timestamp_based synchronization can be utilized not only in the processor unit but also in the sensor units or the channel units or both. In addition, the sensor units need not be connected to the processor unit via respective channel units, but can be connected directly to the processor unit, which can perform all necessary processing. Moreover, as indicated in the power measurement description above, the clock counter need not be situated in a channel unit; the clock counter can be located, e.g., in a sensor unit instead.

What is claimed is:

1. A measurement system comprising
   a first unit that obtains a first measurement value associated with a first time indication and a second measurement value associated with a second time indication; and
   a second unit that comprises a second-unit processor and receives values asynchronously from said first unit, wherein the second-unit processor synchronizes said first and second measurement values in real time using said first and second time indications.

2. The measurement system of claim 1, wherein
   the first unit comprises a first-unit processor that performs a calculation using the first measurement value to generate a refined measurement value associated with a third time indication that is derived from the first time indication; and
   one of the values received by the second unit is the refined measurement value.

3. The measurement system of claim 2, wherein the refined value with the associated third time indication is used as the first measurement value with the associated first time indication when the second-unit processor performs the synchronization.

4. The measurement system of claim 1, wherein the first unit comprises
   a sensor unit to obtain the first measurement value; and
   a channel unit comprising a processor for performing a calculation using the first measurement value.

5. The measurement system of claim 1, wherein the first unit further comprises a clock counter for determining the time indications.

6. The measurement system of claim 1, wherein
   the first unit comprises a first memory and a processor;
   the measurement system comprises a second memory which stores a program usable by the first unit; and
   the processor of said first unit operates according to the program after the program is loaded into said first memory from said second memory.

7. The measurement system of claim 6, wherein the first unit further comprises a non-volatile memory which stores a unique identity code identifying the first unit.

8. The measurement system of claim 7, further comprising a third memory for storing the unique identity code and a description of properties of the first unit.

9. The measurement system of claim 8, further comprising a fourth memory which stores a calculated result derived from said first measurement value.

10. A measurement system comprising
a first measurement unit that obtains a first measurement value associated with a first time indication;
a second measurement unit that obtains a second measurement value associated with a second time indication; and
a processor unit that comprises a processor and receives values asynchronously from said first and second measurement units, wherein the processor synchronizes said first and second measurement values in real time using said first and second time indications.

11. The measurement system of claim 10, wherein
the first measurement unit comprises a first-unit processor that performs a calculation using the first measurement value to generate a refined measurement value associated with a third time indication that is derived from the first time indication; and
one of the values received by the processor unit is the refined measurement value.

12. The measurement system of claim 11, wherein the refined value with the associated third time indication is used as the first measurement value with the associated first time indication when the processor performs the synchronization.

13. The measurement system of claim 10, wherein the first unit comprises
a sensor unit to obtain the first measurement value; and
a channel unit comprising a channel unit processor for performing a calculation using the first measurement value.

14. The measurement system of claim 10, wherein the first measurement unit further comprises a clock counter for determining the time indications.

15. The measurement system of claim 10, wherein
the first measurement unit comprises a first memory and a first-unit processor;
the measurement system comprises a second memory which stores a program usable by the first unit; and
the first-unit processor operates according to the program after the program is loaded into said first memory from said second memory.

16. The measurement system of claim 15, wherein the first measurement unit further comprises a non-volatile memory which stores a unique identity code identifying the first measurement unit.

17. The measurement system of claim 16, further comprising a third memory for storing the unique identity code and a description of properties of the first measurement unit.

18. The measurement system of claim 17, further comprising a fourth memory which stores a calculated result derived from said first measurement value.

19. The measurement system of claim 10, further comprising a clock producing a clock signal wherein both first and second measurement units use said clock signal to produce said time indications.

20. A method of synchronizing measurement values, comprising the steps of
obtaining first and second streams of measurement values,
obtaining, for each measurement value, a time indication representing a time at which said measurement value was obtained, and associating said time indication with said measurement value;
processing said streams of measurement values asynchronously; and
synchronizing said measurement values from said first and second streams in real time by using said time indications.

21. The method of claim 20, wherein measurement values are unprocessed measurement values and the step of processing the streams of measurement values asynchronously comprises the steps of
producing processed measurement values by processing at least one of the streams of unprocessed measurement values; and
determining a new time indication for each processed measurement value and associating said new time indication with said processed measurement value.

22. The method of claim 21, wherein
the new time indication of the processed measurement value is derived from the time indication of at least one of the unprocessed measurement values used to produce the processed measurement value.

23. The method of claim 22, wherein the first stream of unprocessed measurement values is obtained by sampling a measurement parameter of a test subject.

24. The method of claim 23, further comprising a step of associating with the processed measurement value a stream identity indicating the parameter represented by the processed measurement value.

25. A method of synchronizing measurement values, comprising the steps of
obtaining a first stream of measurement values,
obtaining, for each measurement value, a time indication representing a time at which said measurement value was obtained, and associating said time indication with said measurement value;
copying said first stream to produce a second stream of measurement values, and copying said time indications associated with said first stream to produce copied time indications associated with said second stream of measurement values;
processing said streams of measurement values asynchronously; and
synchronizing said measurement values in real time by using said time indications.

26. A method of measuring pulmonary compliance in a subject, comprising the steps of
obtaining a pressure value and an airflow value from the subject;
associating a first time indication with said pressure value and a second time indication with said airflow value;
performing a first calculation using said airflow value to produce a volume value;
associating with said volume value a third time indication derived from said second time indication;
performing a second calculation using said volume value to produce a breath trigger value;
associating with said breath trigger value a fourth time indication derived from said third time indication;
collecting all said values asynchronously;
synchronizing all said values in real time by using said time indications; and
performing a third calculation using all said values to produce a pulmonary compliance value.

* * * * *